(12) United States Patent
Clouatre et al.

(10) Patent No.: US 10,006,079 B2
(45) Date of Patent: Jun. 26, 2018

(54) METHOD FOR ESTABLISHING THE ANTI-DIABETIC POTENTIAL OF BITTER MELON

(71) Applicants: Dallas L. Clouatre, Seattle, WA (US); Daniel E. Clouatre, Seattle, WA (US)

(72) Inventors: Dallas L. Clouatre, Seattle, WA (US); Daniel E. Clouatre, Seattle, WA (US)

(73) Assignee: Glykon Technologies Group, LLC, Seattle, WA (US)

(*) Notice: Subject to any disclaimer, the term of this patent is extended or adjusted under 35 U.S.C. 154(b) by 0 days. days.

(21) Appl. No.: 14/294,547

(22) Filed: Jun. 3, 2014

(65) Prior Publication Data

US 2015/0125887 A1 May 7, 2015

Related U.S. Application Data

(60) Provisional application No. 61/963,511, filed on Dec. 4, 2013.

(51) Int. Cl.
*C12Q 1/54* (2006.01)

(52) U.S. Cl.
CPC ........... *C12Q 1/54* (2013.01); *G01N 2333/39* (2013.01)

(58) Field of Classification Search
None
See application file for complete search history.

(56) References Cited

PUBLICATIONS

Nair et al., International Journal of Pharmaceutical Science Invention, Apr. 2013, vol. 2, Issue 4, p. 12-19.*
Fuangchan et al., Journal of Ethnopharmacology, 2011, Vo. 134, p. 422-428.*
Said et al., eCAM, 2008, vol. 4, p. 421-428.*
Forouhar et al., Journal of Community Hospital Internal Medicine Perspectives, 2012, 2, 18447 (5 pages of PDF), http://dx.doi.org/10.3402/jchimp.v2i2.18447.*
Heinzerling et al., J Chem Educ, Oct. 2012, vol. 89, p. 1582-1586.*
Definition of "container" from Merriam-Webster Online dictionary.*
Anonymous, *Momordica charantia* (bitter melon). Monograph. Altern Med Rev (2007) 12(4):360-363.
Chaturvedi et al., "Effect of Momordica charantia on Lipid Profile and Oral Glucose Tolerance in Diabetic Rats" Phytotherapy Research (2004) 18:954-956.
Cirillo, Vincent P., "Mechanism of Glucose Transport Across the Yeast Cell Membrane" J Bacteriol (1962) 84:485-491.
Ravi et al., "In vitro glucose uptake by isolated rat hemi-diaphragm study of Aegle marmelos Correa root" Bangladesh J Pharmacol (2009) 4:65-68.
Ahmed et al., "Hypotriglyceridemic and hypocholesterolemic effects of anti-diabetic *Momordica charantia* (karela) fruit extract in streptozotocin-induced diabetic rats" Diabetes Research and Clinical Practice 51:155-161 (2001).
Clouatre et al., "Bitter Melon Extracts in Diabetic and Normal Rats Favorably Influence Blood Glucose and Blood Pressure Regulation" Journal of Medicinal Food, 14(12):1496-1504 (2011).
Mirsky et al., "Effects of Insulin and Glucose Tolerance Factor on Glucose Uptake by Yeast Cells" Biol. Signals (1994) 4(3):271-277.

* cited by examiner

*Primary Examiner* — Kade Ariani
(74) *Attorney, Agent, or Firm* — Karl Bozicevic; Bozicevic, Field & Francis LLP

(57) ABSTRACT

A method is disclosed for determining the hypoglycemic potential of *Momordica charantia* (bitter melon) extracts through an in vitro test representative of the range of serum blood sugar typical of normal and diabetic subjects. The in vitro assay provides information on the functional activity of bitter melon extracts for regulating blood glucose uptake in an animal or human.

5 Claims, 3 Drawing Sheets

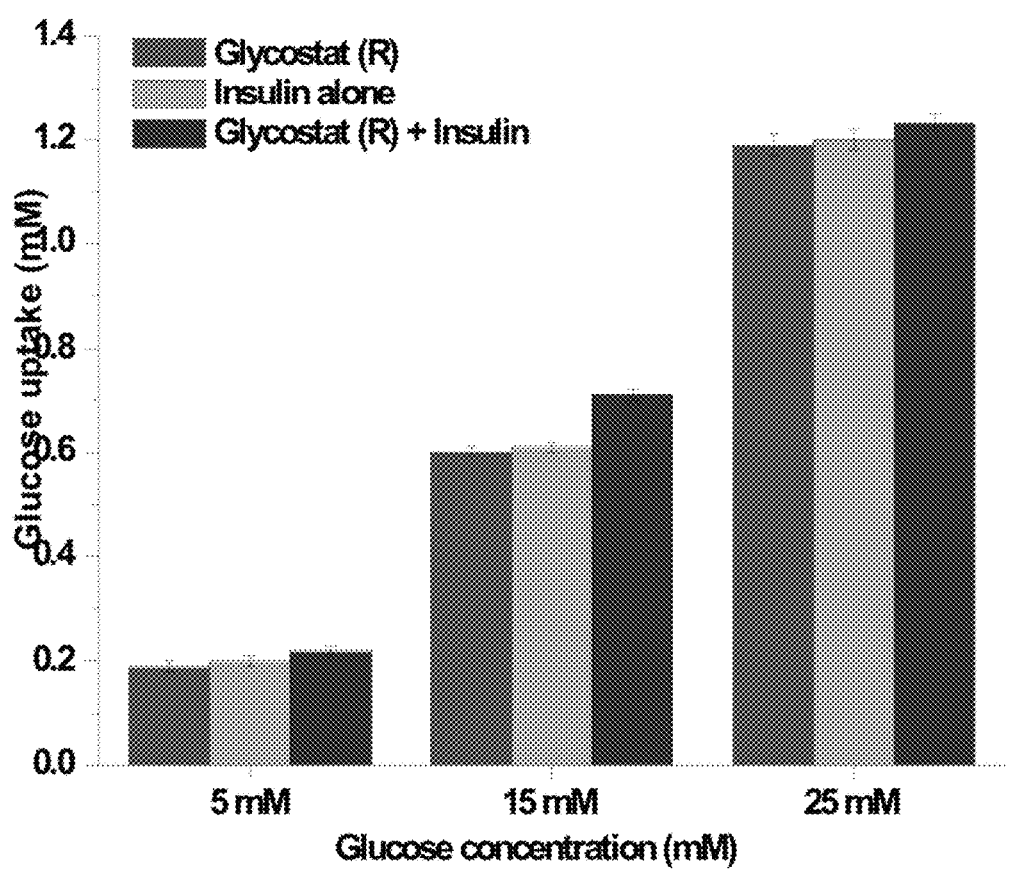
Figure 1. Glycostat®-Hepatocytes

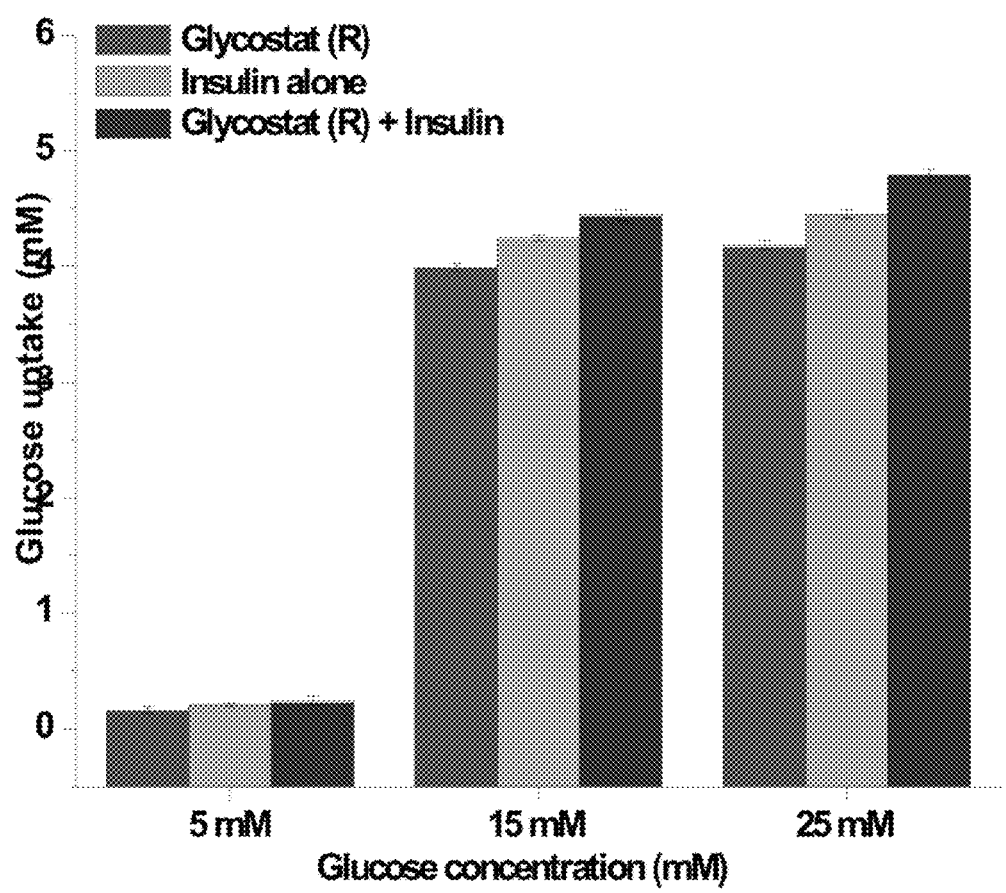
Figure 2. Glycostat®-Cardiomyocytes

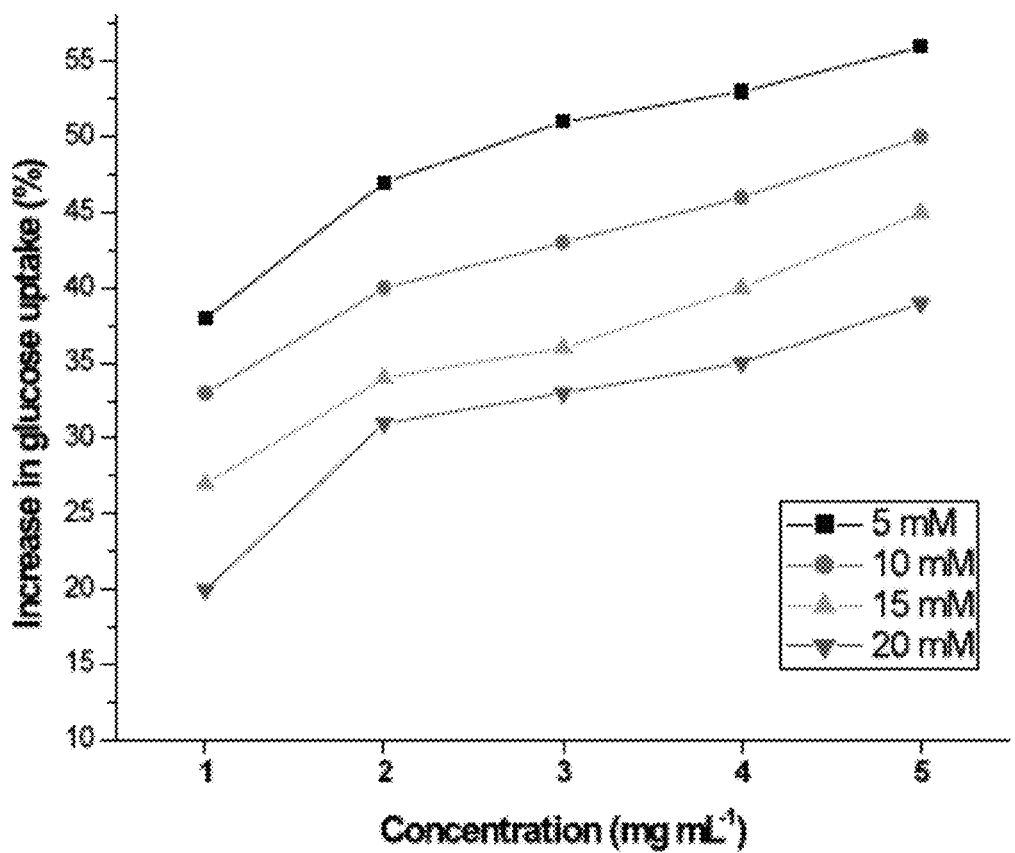
Figure 3. Effect of Glycostat® on glucose uptake in yeast cells

METHOD FOR ESTABLISHING THE ANTI-DIABETIC POTENTIAL OF BITTER MELON

CROSS-REFERENCE

This application claims the benefit of U.S. Provisional Application No. 61/963,511, filed Dec. 4, 2013, which application is incorporated herein by reference.

FIELD OF THE INVENTION

This invention relates to a method for determining the hypoglycemic potential of *Momordica charantia* (bitter melon) extracts through an in vitro test representative of the range of serum blood sugar typical of normal and diabetic subjects.

BACKGROUND OF THE INVENTION

Elevated and erratic blood sugar levels are components of the condition known as diabetes mellitus. This condition can be life-threatening and high glucose levels in blood plasma (hyperglycemia) can lead to a number of conditions caused by chronic diabetes, for example, atherosclerosis, microangiopathy, peripheral neuropathy, kidney disorders and renal failure, cardiac disease, diabetic retinopathy and other ocular disorders, including blindness. A precursor to diabetes, insulin resistance, may be a component in many age-related deteriorations and can result in alternating periods of both high and low blood sugar, uneven energy, obesity, hypertension and other disorders.

Diabetic conditions usually are treated medically in one of two ways. Insulin, the hormone which removes glucose from circulation, is supplied exogenously to treat the more severe cases in which the body's ability to produce this hormone is either impaired or nonexistent. Oral diabetes medications (such as sulphonylureas and biguanides) are also available. The drug metformin, a biguanide which is perhaps the safest and most successful of the usual oral hypoglycaemics, suppresses an elevated rate of basal hepatic glucose production. This mode of action in one of the more successful hypoglycaemic drugs underscores the fact that the inability to regulate and suppress hepatic glucose production is an important aspect of diabetes and prodiabetic conditions.

*Momordica charantia* Linn. (Cucurbitaceae), is commonly known as bitter melon, bitter gourd, karela, and pare. It grows in tropical areas of the Amazon, East Africa, Asia, India, South America, and the Caribbean and is used traditionally as both food and medicine. The plant is a climbing perennial with elongated fruit that resembles a warty gourd or cucumber. The unripe fruit is white or green in color and has a bitter taste that becomes more pronounced as the fruit ripens. The seeds, fruit, leaves, and root of the plant have been used in traditional medicine for microbial infections, sluggish digestion and intestinal gas, menstrual stimulation, wound healing, inflammation, fever reduction, hypertension, and as a laxative and emetic (Anonymous, 2007). Clinical conditions for which *M. charantia* extracts (primarily from the fruit) are currently being used include diabetes, dyslipidemia, microbial infections, and potentially as a cytotoxic agent for certain types of cancer (Oishi et al., 2007; Chaturvedi et al., 2004). An emerging body of evidence indicates that bitter melon in the form of non-hybridized or "wild" varieties exerts more powerful anti-diabetic effects than do modern cultivated varietals (Clouatre et al., 2011).

The primary constituents thought to be responsible for the hypoglycemic properties of *M. charantia* include charantin, insulin-like peptides, cucurbutanoids, momordicin, and oleanolic acids. *M. charantia* also has numerous other constituents including proteins, glycosides, saponins, and minerals (Ahmed et al., 2001; Harinantenaina et al., 2006; Clouatre et al., 2011). Extracts commonly are defined in terms of percentages of one or more of these active ingredients. However, controversy surrounds claims regarding the active principles of bitter melon. According to various authorities, the most prominent proposed active ingredients either have no clear quantitative relationship to physiologic effects or lack any worth for the treatment of blood sugar issues. For instance, some authorities deny that charantin exhibits any benefits whatsoever (Clouatre et al., 2011).

Bitter melon extracts also are notoriously unstable. The fresh fruit, the freshly expressed juice of the fruit, and freshly prepared extracts from the fresh fruit generally have been successful in animal and clinical trials. Nevertheless, prepared powdered extracts such as typically are characterized by charantin or bitters content seldom have demonstrated hypoglycemic efficacy.

The lack of efficacy of most prepared bitter melon extracts and the demonstrable unreliability of characterizations by the content of major constituents, such as charantin and bitters, in describing functional activity indicates a clear need for a reliable means of determining physiologic activity. Similarly, the instability of most extracts over time strongly indicates the need for a technique for quickly determining efficacy without having to resort to time-consuming and expensive animal or clinical trials at every point to determine potency. An in vitro test of functional efficacy is needed to allow for determining batch-by-batch performance and to improve upon the current extraordinarily spotty record of bitter melon extracts.

SUMMARY OF THE INVENTION

The invention uses specific in vitro tests to reliably establish the activity of bitter melon and its extracts as hypoglycemic agents. Further, the invention validates the range of activity in relation to the range of blood glucose exhibited by non-diabetic and diabetic individuals. The activity of a bitter melon extract is characterized as (1) directly proportional to the sample concentration, and (2) inversely proportional to the molar concentration of glucose. Bitter melon and its extracts are functionally characterized on a batch-by-batch basis for its hypoglycemic potential. The method of the invention solves the problem of charantin and/or other bitter melon components often used for standardization of products not exhibiting a clear or consistent relationship to hypoglycemic activity.

It is an objective of the present invention to provide a method of for treating or ameliorating diabetes or insulin resistance by providing a means of reducing elevated blood sugar levels.

It is a further object of the present invention to provide a means of stabilizing blood sugar levels so as to avoid reactive hypoglycemia and to otherwise improve blood sugar metabolism.

The present invention allows for the use of forms of bitter melon as anti-diabetics agents, for lowering elevated blood sugar levels, and for stabilizing fluctuating blood sugar levels.

A further advantage of the present invention is to allow the employment of effective amounts of bitter melon and its extracts for weight loss and other purposes related to blood glucose regulation.

Another aspect of the invention is an in vitro assay which predicts the efficacy of forms of bitter melon extracts for influencing cellular uptake of blood sugar and, in turn, blood sugar regulation. The assay provided here is an unexpected discovery based on a series of experiments that demonstrated a relationship between results in live animals, effects in different types of animal cells (liver cells and cardiomyocytes, i.e., heart muscle cells) and then effects in a yeast cell model. The in vitro yeast cell model was found to adequately represent in vivo glucose disposal in an animal model.

These and other objects, advantages, and features of the invention will become apparent to those persons skilled in the art upon reading the details of the methods and assays as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1 is a bar graph showing the relationship between glucose uptake and glucose concentration with respect to three different test items at three different concentrations each as carried out on hepatocytes of rats.

FIG. 2 is a bar graph comparing glucose uptake to glucose concentration for three different items at three different concentrations as carried out on cardiomiocytes of rats.

FIG. 3 is a line graph showing increases in glucose uptake relative to concentration for Glycostat® at four different concentrations on yeast cells.

DETAILED DESCRIPTION OF THE INVENTION

Before the present methods and assays are described, it is to be understood that this invention is not limited to particular compounds, mixtures or steps described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a test compound" includes a plurality of such compounds and reference to "the test" includes reference to one or more tests and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

An in vitro assay for testing the ability of the compound or group of compounds to enhance glucose uptake is disclosed. The method comprises adding a known amount and/or concentration of glucose to a yeast cell system. Thereafter adding a test compound such as bitter melon extracts to the yeast/glucose environment. After allowing time to pass such as a time period in the range of 5 minutes to 12 hours or 10 minutes to 5 hours or 1 hour to 4 hours. After allowing time to pass testing the environment for the presence of glucose and comparing the concentration of glucose detected to the concentration of glucose originally present.

The yeast cell assay provides an in vitro assay for testing the ability of compounds such as bitter melon extracts to enhance glucose uptake. By comparing the ability of the melon extract to enhance glucose uptake it is possible to determine dosing of a patient with bitter melon in order to treat the patient with respect to abnormally high glucose levels.

In accordance with the method a closed environment of yeast cells is utilized. A known amount and as such a known concentration of glucose is added to the yeast cells and the time of adding the glucose is noted. Thereafter a test compound such as bitter melon extract is added to the closed environment, the time is noted and after a given period of time the amount and concentration of glucose in the closed environment is determined. The differential between the initial concentration of glucose and the glucose concentration after adding the bitter melon extract is determined after a known period of time passes. That differential is an indication of the hypoglycemic potential of the test compound or bitter melon extract. The differential can be compared to known standards. Accordingly, the hypoglycemic potential of the tested compound such as the bitter melon extract can be determined and used in labeling products. Those products can be used to dose patients and in particular used to dose diabetic patients.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

An initial trial was undertaken to determine the efficacy of different bitter melon extracts in normal and diabetic rats and, in light of the findings, to chose a candidate extract for further experiments. This and related experiments subsequently were published (Clouatre et al., 2011.) Wistar Albino male rats 12 weeks of age were obtained from St John's Pharmacy College Animal House, India and handled according to institutional practices. Rats were divided into eight groups of six rats housed six to a cage with an average weight of 175 to 225 grams per group. All rats were fed a standard rat chow diet ad libitum from Sai Durga Feed, Bangalore; water also was supplied ad libitum. Following 7 days acclimatization, one half of the rats were fasted for 24 hours and then injected with freshly prepared STZ in citrate buffer [pH 7.4] (45 mg/kg, i.p). After one week, rats with marked hyperglycemia (fasting blood glucose >300 mg/dL) were used as the diabetic rats.

Test materials were four different extracts (as dry powders) of bitter melon of a wild genotype or metformin. Extracts 1-4 were produced and preserved via different methods attempting to retain efficacies reported for macerated fresh fruit preparations. EX-1 was a vacuum-dried powder of the macerated extract of fresh fruit (~25:1). EX-2 was a freeze-dried powder of the macerated extract of fresh fruit (~25:1). EX-3 was a spray-dried powder of the macerated extract of fresh fruit (~25:1). EX-4 was a vacuum-dried powder of the macerated extract of fresh fruit adsorbed onto powdered vacuum-dried fresh fruit (~15:1). Dosages of the extracts (mg/kg bodyweight/day) were 50 and 250 mg/kg as indicated. After an overnight fast, the extract samples suspended in 5% gum acacia were administered to the animals by gastric intubations with a syringe.

For test purposes, glucose was given orally by intubation as a 40% solution (1 g/kg body wt). Blood samples following the glucose challenge were collected for the measurement of blood glucose from the tail vein at 0, 1, 2, 3 and 4 hrs. The blood glucose level was determined by using an electronic glucometer (Accu Check, Roche Diagnostic).

First, the hypoglycemic activity of bitter melon extracts was studied in normal rats. The drug metformin was used as the positive control (Table 1). The experiment revealed that the two examined extracts, EX-1 and EX-2, reduced normal blood sugar levels, but the reduction was less than that with metformin. Significantly and unlike metformin, the bitter melon extracts did not result in hypoglycemia in normal animals (glucose <70 mg/dL in this model).

Next, the anti-hyperglycemic activity of bitter melon extracts was studied in streptozotocin-induced diabetic rats described above. Metformin was used as the positive control drug (Table 2). The fasting blood glucose level of the diabetic animals was significantly reduced (P<0.01) compared to initial levels of blood glucose (0 h) in the respective groups. The reduction of blood glucose levels by the bitter melon extracts in general was comparable to metformin, with the more efficacious extracts (EX-1 and EX-4) being stronger than metformin at the relative dosages administered, especially at 4 hours.

In normal rats, wild bitter melon extracts administered at 50 mg/kg body weight lowered blood sugar for approximately 4 hours without inducing hypoglycemia in contrast to metformin, which at 50 mg/kg led to hypoglycemia. In diabetic animals, two of the extracts administered at the rate of 250 mg/kg proved comparable to metformin administered at the rate of 150 mg/kg. At 4 hours, all extracts significantly reduced glucose in comparison with initial starting levels. EX-1 and EX-4 reduced blood glucose 66.56 and 63.42 percent (mg %), respectively, compared with metformin's 53.52 percent at 4 hours. There was no statistical difference between either EX-1 or EX-4 and metformin.

TABLE 1

Effect of EX-1 and EX-2 on Blood Glucose Levels (mg %) in Normal Rats

| Treatment | Dose (mg/kg) | Initial (0 hr) | +1 hr | +2 hr | +3 hr | +4 hr |
|---|---|---|---|---|---|---|
| EX-1 | 50 | 92.3 ± 1.7 | 81.2 ± 3.4* (12.1) | 78.7 ± 2.2* (14.8) | 83.8 ± 3.5 (9.2) | 87.2 ± 2.6 (5.5) |
| EX-2 | 50 | 89.0 ± 2.4 | 79.2 ± 0.8* (11.1) | 79.7 ± 0.6* (10.5) | 81.3 ± 2.0* (2.7) | 86.5 ± 2.4 (2.8) |
| Metformin | 50 | 93.3 ± 1.3 | 85.5 ± 1.8 (17.5) | 73.5 ± 1.2* (34.9) | 66.5 ± 1.2* (46.4) | 52.5 ± 0.7* (53.5) | n=6 animals in each group. Values in parentheses indicate percent reduction in blood sugar level (*P<0.01) compared with initial glucose value (0 h) in the respective group. Note that Metformin at 3 h and 4 h resulted in hypoglycemia in normal animals.

TABLE 2

Effects of EX-1, EX-2, EX-3 and EX-4 on Blood Glucose Levels [mg %] in Diabetic Rats

| Treatment | Dose (mg/kg) | Initial (0 hr) | +1 hr | +2 hr | +3 hr | +4 hr |
|---|---|---|---|---|---|---|
| EX-1 | 250 | 312.5 ± 39.6 | 255.8 ± 32.0 (18.13) | 225.2 ± 23.3* (27.9) | 176.2 ± 7.7* (43.6) | 104.5 ± 8.3* (66.6) |

TABLE 2-continued

Effects of EX-1, EX-2, EX-3 and EX-4 on Blood Glucose Levels [mg %] in Diabetic Rats

| Treatment | Dose (mg/kg) | Initial (0 hr) | Treatment | | | |
|---|---|---|---|---|---|---|
| | | | +1 hr | +2 hr | +3 hr | +4 hr |
| EX-2 | 250 | 303.3 ± 33.7 | 215.3 ± 14.5* (29.01) | 188.0 ± 17.7* (38.0) | 164.5 ± 18.4* (45.8) | 154.8 ± 22.7* (49.0) |
| EX-3 | 250 | 319.7 ± 18.6 | 252.5 ± 13.9* (21.0) | 215.0 ± 11.0* (32.6) | 193.8 ± 4.2* (39.4) | 173.3 ± 2.9* (45.7) |
| EX-4 | 250 | 322.2 ± 23.8 | 245.3 ± 27.6 (23.8) | 195.5 ± 6.2* (39.0) | 179.0 ± 12.7* (44.4) | 117.8 ± 8.5* (63.4) |
| Metformin | 150 | 329.2 ± 5.3 | 271.6 ± 4.0 (17.5) | 214.4 ± 3.2* (34.9) | 176.0 ± 6.7* (46.4) | 153.0 ± 3.3* (53.5) | n=6 animals in each group. Values in parentheses indicate percent reduction of blood sugar level (*P<0.01) compared with initial level of blood glucose (0 h) in the respective group.

Example 2

The results of Example 1 determined the candidate extract for subsequent experiments and demonstrated efficacy in both normal and diabetic models. These in vivo findings, however, did not elucidate the nature of the bitter melon activity. Bitter melon is the source of a large number of putatively active compounds and questions abound as to the nature of this activity. One possible source of activity is inhibition of alpha-amylase, a digestive enzyme for carbohydrates found in the gastrointestinal tract. More interesting and also potentially far more important for blood sugar regulation is the direct action of bitter melon on cellular receptors. The present Example was designed to determine the level of activity of the extract from Example 1 in an in vitro model using rat hepatocytes inasmuch as the liver is one of the primary sites of glucose disposal. That extract, identified by its registered trade name Glycostat®, was tested by itself, versus insulin and in conjunction with insulin. FIG. 1 shows that Glycostat® was as effective as insulin in stimulating glucose transport into liver cells. Furthermore, in combination with insulin, Glycostat® enhanced the glucose uptake to a significant extent. These results suggest both insulin mimetic and insulin sensitizing activity for Glycostat®. (Results are based on the method of Ravi et al., 2009, with modifications.)

Example 3

The primary site of glucose disposal typically is lean muscle tissue. In this example rat cardiomyocytes (heart muscle cells) were used to determine the activity of the extract of Example 1 in muscle cells. Again, as in Example 2, Glycostat® was as effective as insulin in stimulating glucose transport into cells. In combination with insulin, Glycostat® enhanced the glucose uptake to a significant extent. The results shown in FIG. 2 demonstrate both insulin mimetic and insulin sensitizing activity for Glycostat®. (Results are based on the method of Ravi et al., 2009, with modifications.)

Example 4

The previous experiments demonstrated that a bitter melon extract with marked in vivo activity is characterized by direct cellular effects in both liver and muscle cells. Glucose transport across the yeast cell membrane (Cirillo V, 1962) in the current Example was used as an in vitro screening method for the hypoglycemic effect of the extract from Example 1. The characteristics of glucose transport in the presence/absence of the extract are presented in FIGS. 1-3, and FIG. 3 provides data on yeast cells. The increase in the glucose uptake by Glycostat® ranged between 20-58%. The concentration of 5-20 mM represents the blood glucose concentrations of 90-400 mg dL$^{-1}$ and hence serves as an indicator of in vivo blood sugar ranging from normal through diabetic conditions. It was observed that the increase in glucose uptake by Glycostat® was directly proportional to the sample concentration and inversely proportional to the molar concentration of glucose. This information is particularly useful in a dose optimization process wherein, depending on the blood glucose concentration, the dosage can be adjusted. $EC_{50}$ values can be utilized for this purpose. ($EC_{50}$ may be defined as the molar concentration of an agonist that produces 50% of the maximum possible response/effect for that agonist.)

CONCLUSIONS

The lack of efficacy of most prepared bitter melon extracts and the demonstrable unreliability of characterizations by the content of major constituents, such as charantin and bitters, in describing functional activity indicates a clear need for a reliable means for determining physiologic effects without having to resort to in vivo tests, which necessarily are slow and expensive. The inventors have discovered that an in vitro test utilizing a yeast cell model can usefully determine the increase in glucose uptake by bitter melon extracts. In this model, the results are directly proportional to the sample concentration and inversely proportional to the molar concentration of glucose. The invention can be used to determine the functional efficacy of extracts on a batch-by-batch basis.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. An in vitro assay method, comprising:
   (a) adding to a closed environment yeast cells a known amount of glucose to obtain a known concentration of glucose;
   (b) adding a known amount of extract of *Momordica charantia* obtained from a first batch of *Momordica charantia* to the closed environment of yeast cells to provide a known concentration of the extract of *Momordica charantia* in the closed environment;
   (c) waiting a period of time after adding the extract of *Momordica charantia* for glucose uptake by the yeast cells;
   (d) determining a second glucose concentration in the closed environment of yeast cells;
   (e) comparing the known glucose concentration in step (a) to the second glucose concentration in step (d);
   (f) determining a differential between the known glucose concentration and the second glucose concentration for the first batch of *Momordica charantia*; and
   (g) repeating steps (a)-(f) with a second batch of extract of *Momordica charantia* thereby determining a second differential for the second batch of extract of *Momordica charantia*, and comparing the differential determined for each batch to a known standard thereby determining the hypoglycemic potential of the extract of *Momordica charantia*.

2. The method of claim 1, further comprising: using the differential determined in step (g) for each batch to optimize dosing of a subject with the extract of *Momordica charantia*.

3. The method of claim 1, further comprising:
   using the differential to optimize dosing of a subject with the extract.

4. The method of claim 1, further comprising: repeating steps (a)-(f) a plurality of times with extracts obtained from different batches of *Momordica charantia* to make a batch-by-batch comparison of the differential determined for each batch to optimize dosing of a subject with the extract of *Momordica charantia*.

5. An in vitro assay method, comprising:
   (a) adding to a closed environment of yeast cells a known amount of glucose to obtain a known concentration of glucose;
   (b) adding a known amount of extract of *Momordica charantia* obtained from a first batch of *Momordica charantia* to the closed environment of yeast cells to provide a known concentration of the extract of *Momordica charantia* in the closed environment;
   (c) waiting a period of time after adding the extract of *Momordica charantia* for glucose uptake by the yeast cells;
   (d) determining a second glucose concentration in the closed environment of yeast cells;
   (e) comparing the known glucose concentration in step (a) to the second glucose concentration in step (d);
   (f) determining a differential between the known glucose concentration and the second glucose concentration for the first batch of extract of *Momordica charantia*;
   (g) repeating steps (a)-(f) a plurality of times with extract obtained from different batches of *Momordica charantia* to make a batch-by-batch comparison of the differential determined from each batch; and using the differential to optimize dosing of a subject with the extract of *Momordica charantia*.

* * * * *